United States Patent [19]
Papa et al.

[11] Patent Number: 6,162,802
[45] Date of Patent: Dec. 19, 2000

[54] SYNERGISTIC COMBINATION THERAPY USING BENAZEPRIL AND AMLODIPINE FOR THE TREATMENT OF CARDIOVASCULAR DISORDERS AND COMPOSITIONS THEREFOR

[76] Inventors: Joseph Papa, Muhlebachweg 19, Allschwil, Switzerland; Marc M. J. Henis, 9 Glen Rd., Randolph, N.J. 07869

[21] Appl. No.: 07/848,816

[22] Filed: Mar. 10, 1992

[51] Int. Cl.$^7$ .......................... A61K 31/55; A61K 31/44
[52] U.S. Cl. .......................... 514/213; 514/356; 514/824; 514/866
[58] Field of Search .................................. 514/213, 356, 514/824, 866

[56] References Cited

U.S. PATENT DOCUMENTS

| | | | |
|---|---|---|---|
| 4,410,520 | 10/1983 | Watthey | 424/244 |
| 4,572,909 | 2/1986 | Campbell et al. | 514/356 |
| 4,703,038 | 10/1987 | Garthoff et al. | 514/19 |
| 4,871,731 | 10/1989 | Walker | 514/211 |
| 4,879,303 | 11/1989 | Davison | 514/356 |
| 4,931,430 | 6/1990 | Sudilovsky et al. | 514/19 |
| 5,037,821 | 8/1991 | Horovitz | 514/211 |
| 5,093,129 | 3/1992 | Horovitz et al. | 424/451 |
| 5,098,910 | 3/1992 | Becker et al. | 514/299 |

FOREIGN PATENT DOCUMENTS

| | | |
|---|---|---|
| 259838 | 3/1988 | European Pat. Off. . |
| 288732 | 11/1988 | European Pat. Off. . |
| 321221 | 6/1989 | European Pat. Off. . |
| 180785 | 7/1989 | European Pat. Off. . |
| 331803 | 9/1989 | European Pat. Off. . |
| 334264 | 9/1989 | European Pat. Off. . |
| 344995 | 12/1989 | European Pat. Off. . |
| 379351 | 7/1990 | European Pat. Off. . |
| 381074 | 8/1990 | European Pat. Off. . |
| 381075 | 8/1990 | European Pat. Off. . |

OTHER PUBLICATIONS

Clozel, "Effects of Nitrendipine and Cilazapril Alone or in Combination on Hemodynamics and Regional Blood Flows in Conscious Spontaneously Hypertensive Rats," *J. Cardiovas. Pharm.*, vol. 12, No. 5, pp. 600–07 (1988).

Burges et al, *Cardiovas. Drug Dev* 8 (1) 25–44, 1990 (Abstract).

Clozel, *J. Cardiovas. Pharm.* 1988, 12(5), 600–607 (Abstract).

Dahlof et al, *J. Cardiovas Pharm* 1988 12, Supp 6 p. S104–108 (Abstract).

Zanchetti, J.*Cardiovas. Pharm.*, 1988, 12 Supp. 4 p. S80–85 (Abstract).

Baba et al,*Diabetologia* Jan. 1989, 32(1) p. 40–44 (Abstract).

Maclean et al, *J. Hum. Hypertens.* Aug. 1988, 2(2) p. 127–132 (Abstract).

Dundee, *J. Cardiovas. Pharmacol*1988, 12 Supp 7, p. S85–88 (Abstract).

Bellet et al,*Br. J. Clin. Pharmac.* 1987, 24, 465–472.

Ikram et al, *J. Amer. Coll. Cardiol.* 17(2) 188A, 1991 Abstract.

Smith et al, *FASEB* vol. 5, No. 4, Mar. 11, 1991, p. A851, Abstract #2795.

*Primary Examiner*—Kimberly Jordan
*Attorney, Agent, or Firm*—Diane Tso; Thomas Hoxie

[57] ABSTRACT

A method for the treatment of a variety of cardiovascular disorders and related conditions in a mammal having at least one such disorder or condition is disclosed comprising treating the mammal with cotherapy comprising benazepril and amlodipine or pharmaceutically acceptable salts of either or both. Combination formulations of benazepril and amlodipine for use in the method are also disclosed.

33 Claims, No Drawings

SYNERGISTIC COMBINATION THERAPY USING BENAZEPRIL AND AMLODIPINE FOR THE TREATMENT OF CARDIOVASCULAR DISORDERS AND COMPOSITIONS THEREFOR

FIELD OF THE INVENTION

The present invention relates to cardiovascular disease states, whether the underlying problem is cardiovascular in nature or secondary to some other condition, and their treatment. It further relates to the treatment of underlying cardiovascular problems which lead to, or present as, non-cardiovascular disease states as well. In addition, the invention relates to angiotensin coverting enzyme inhibitors (ACEI) and the conditions for which treatment therewith is known to be useful. Still further, the invention relates to calcium channel blockers (CCB) and the conditions for which treatment therewith is known to be useful. More specifically, the invention is concerned with the field of combination therapy of an ACEI and a CCB.

BACKGROUND OF THE INVENTION

Cardiovascular disease treatment has evolved rapidly over the last few decades from the early diuretics and natural products such as rauwolfia serpentina to the newest agents such as angiotensin converting enzyme inhibitors (ACEI) of the last few years and the even more recent calcium channel blockers (CCB). In efforts to achieve improved therapy (primarily for the treatment of hypertension, its sequelae, reversible conditions secondary to hypertension, and hypertension secondary to other conditions), a number of agents in each of these classes have been tested both alone as well as in combination with other agents. Some of the conditions for which at least one of these agents has been used or is believed useful include, without limitation, hypertension, angina, myocardial infarction, atherosclerosis, diabetic nephropathy, diabetic cardiac myopathy, renal insufficiency, peripheral vascular disease, left ventricular hypertrophy, cognitive dysfunction, stroke, and headache. Others will be apparent to those of ordinary skill in the art based on a knowledge of the underlying mechanisms involved as well as on general clinical and pre-clinical experience.

Benazepril, benazeprilat, and their pharmaceutically acceptable salts are disclosed in U.S. Pat. No. 4,410,520, along with pharmaceutically acceptable dosage forms thereof, dosage ranges and suitable routes of administration therewith, and uses therefor, all of which are incorporated herein by reference. Amlodipine and its pharmaceutically acceptable salts are set forth in U.S. Pat. No. 4,572,909, incorporated herein by reference. Phamaceutically acceptable dosage forms, dosage ranges, suitable routes of administration, and uses of amlodipine and its salts are set out there. U.S. Pat. No. 4,879,303 is directed to the besylate salt of amlodipine, and it too is incorporated herein by reference. More specific dosages, routes of administration, formulations, and uses for amlodipine besylate can be found there. An excellant review of amlodipine is Burges et al, Cardiovas Drug Dev. 8(1) 25–44, 1990.

Recently, particular combinations of an ACEI and a CCB have appeared in the literature. See generally for example EP 334,264 A2 (corresponding to U.S. application Ser. No. 171,068, filed Mar. 21, 1988), EP 180,785-B and EP 257, 485; J. Cardiovas. Pharm 1988, 12(5) p.600–607; J. Cardiovas. Pharm, 1988, 12, Suppl 6, p.S104–108 and Suppl 4, p.S80–85; and Diabetologia 1/89 32(1), p.40–44. More specific references which have appeared include: J. Hum. Hypertens. Aug 1988 2(2) p.127–132 and J. Cardiovas Pharmacol 1988 12 Suppl 7 p S85–88, each of which discloses combination usage of amlodipine with captopril; and Br. J. Clin. Pharmac. 1987, 24, 465–472, disclosing combination usage of benazepril and nicardipine; and J. Amer. Coll. Cardiol. 17 (2) 188A, 1991, disclosing combination usage of benazepril and nifedipine. In this last reference, the authors conclude that there is no advantage in combining benazepril and nifedipine over the use of nifedipine alone. Hence, the art has mixed teachings as to the benefits of combination therapy between ACEIs and CCBs generally, and especially with the use of benazepril as the ACEI in such combinations.

OBJECTS OF THE INVENTION

It is an object of the invention to provide a synergistic combination therapy for the treatment of cardiovascular diseases and their sequelae which are responsive to antihypertensive therapy.

It is another object of the invention to provide combination products suitable for carrying out the aforementioned object.

SUMMARY OF THE INVENTION

Surprisingly, these and other objects of the present invention are accomplished by a method of treating a condition responsive to co-therapy with an angiotensin converting enzyme inhibitor (ACEI) and a calcium channel blocker (CCB), in a mammal in a need thereof comprising administering to said mammal cotherapy of (1) an ACEI selected from the group consisting of benazepril, benazeprilat, and pharmaceutically acceptable salts thereof, and (2) A CCB selected from the group consisting of amlodipine and pharmaceutically acceptable salts thereof, said ACEI and said CCB being administered in synergistically effective amounts to treat said condition.

DETAILED DESCRIPTION OF THE INVENTION

More specifically, the invention is a method of treating a condition responsive to co-therapy with an angiotensin converting enzyme inhibitor (ACEI) and a calcium channel blocker (CCB), said condition selected from the group consisting of hypertension, angina, myocardial infarction, atherosclerosis, diabetic nephropathy, diabetic cardiac myopathy, renal insufficiency, peripheral vascular disease, left ventricular hypertrophy, cognitive dysfunction, stroke, and headache, in a mammal in need thereof comprising administering to said mammal cotherapy of (1) an ACEI selected from the group consisting of benazepril, benazeprilat, and pharmaceutically acceptable salts thereof, and (2) a CCB selected from the group consisting of amlodipine and pharmaceutically acceptable salts thereof, said ACEI and said CCB being administered in synergistically effective amounts to treat said condition.

Preferably, the ACEI is benazepril or a salt thereof, most preferably a salt thereof. Suitable salts of benazepril and benazeprilat can be found in U.S. Pat. No. 4,410,520 mentioned above. For purposes of the present invention, the hydrochloride salt of the ACEI is most advantageous, with the most prefered specific ACEI compound being benazepril hydrochloride.

The present invention CCB is limited to amlodipine or its salts, which are set forth in the above cited U.S. Pat. No. 4,572,909, with the most suitable salt being the besylate salt (the subject matter of U.S. Pat. No. 4,879,303).

While the ACEI and the CCB can be administered at different times, they are most preferably administered at the same time. Most conveniently, this is via a single, fixed combination dosage form. However, the ACEI can be administered at times different from the administration of the CCB and the invention benefits still be realized. When administered at different times, the ACEI and the CCB should be given within about 16 hours of each other, preferably within about 12 hours of each other, more preferably within about 8 hours of each other, most preferably within about 4 hours of each other. Of course, these time periods can be extended if the dosage form is one which will "administer" the agents for extended periods.

When the ACEI and the CCB are given substantially simultaneously, they may be given by a single fixed combination dosage form or by different dosage forms, whichever is convenient. When given by different dosage forms, it is irrelevant whether the route of administration is the same for each agent or different for each agent. Any route of administration known for the individual agents is acceptable for the practice of the present invention. Most preferably, the agents are given in a fixed combination, or at least substantially simultaneously, i.e. within about 1 hour of each other. Also, the most suitable dosage form is an oral dosage form, where oral administration is a clinically suitable route.

Dosages of the two agents include all dosages at which the agents are used individually. Typically, the dosage of the ACEI is from about 2 to about 80 mg, preferably about 3 to about 40 mg, more preferably about 5 to about 20 mg (based on benazepril hydrochloride). Generally the dosage of the CCB is about 1 to about 20 mg, more preferably about 2 to about 10 mg, more preferably about 2.5 to about 5 mg (based on amlodipine free base). Corresponding dosages for other salts of amlodipine, for free benazepril and other salts of benazepril, and benazeprilat and its salts will be readily apparent to those of ordinary skill in the art. In each of the dosages set forth here, the range is the acceptable range based an adult mammal of approximately 50 to about 70 kg. Modified dosage ranges for mammals of other sizes and stages of development will be apparent to those of ordinary skill. In the practice of the present invention, the weight ratio of the ACEI to CCB (based upon benazepril hydrochloride-:amlodipine free base) is from about 0.5:1 to about 10:1, more preferably 1:1 to 8:1. The precise weight ratios when using salts other than those set forth above may change, but only because the corresponding amount of the active agents have different weights. Those of ordinary skill in the art will be able to make the appropriate calculations. Particularly advantageous ratios of benazepril hydrochloride:amlodipine free base are 1:1, 2:1, 4:1, and 8:1.

Benazepril and amlodipine are physically incompatible substances. Hence, if incorporated into a single dosage form they must be kept physically separated. This may be accomplished in any of the myriad ways known in the art, such as bi-layered tablets, coated pellets of one agent incorporated into a tablet of the other, separately coated pellets of each agent in a capsule or tablet, coated pellets of one agent in capsule together with powder of the other agent, each agent microencapsulated separately and then blended together for use in a tablet or capsule, use of a dual or multiple compartment transdermal device, etc. Due to the incompatibility, combination products of the two agents in an injectable solution are not really acceptable. For convenience purposes, a coated compressed tablet of benazepril together with amlodipine powder in a capsule has been found to be the most desirable oral form.

For purposes of the present invention, the synergy referred to throughout this description relates primarily to blood pressure, either systolic or diastolic, or both. The conditions for which the instant invention is useful includes, without limitation, hypertension (whether of the malignant, essential, reno-vascular, diabetic, isolated systolic, or other secondary type), congestive heart failure, angina (whether stable or unstable), myocardial infarction, atherosclerosis, diabetic nephropathy, diabetic cardiac myopathy, renal insufficiency, peripheral vascular disease, left ventricular hypertrophy, cognitive dysfunction (such as Alzheimer's, etc), stroke, headache, and life extension.

For the present purposes, preferred mammals are rabbits, dogs, goats, hogs, sheep, horses, cattle, and primates, more preferably primates, most preferably humans.

EXAMPLES

The following examples are presented to exemplify, but not to limit the invention.

Example 1

One thousand capsules containing 20 mg of benazepril hydrochloride and amlodipine besylate equivalent to 5 mg of amlodipine base for use in the present invention were prepared as follows:

Benazepril hydrochloride cores are prepared using the following:

| | |
|---|---|
| 1. Benazepril HCL | 20.000 g |
| 2. Lactose, monohydrate | 32.920 g |
| 3. Pregelatinized Starch | 5.000 g |
| 4. Colloidal $SiO_2$ | 1.000 g |
| 5. Crospovidine | 2.000 g |
| 6. Microcrystalline Cellulose | 10.000 g |
| 7. Hydrogenated Castor Oil | 4.000 g |
| 8. Purified Water | as needed |

Components 1–3 are milled and blended together and water is added to granulate the blend. The wet granules are screened and oven dried. The dried granules are then milled together with components 5–7. Component 4 is screened and then mixed with the other ingredients. The resulting mixture is then compressed into a core.

The thus made cores are coated with a coating solution prepared as follows:

| | |
|---|---|
| 9. Hydoxypropyl Methylcellulose 2910, 3 cps | 4.881 g |
| 10. Polysorbate 80 | 0.119 g |
| 11. Purified Water | as needed |
| 12. Talc | trace |

Component 10 is dissolved in the water and component 9 is added thereto. The previously made cores are then coated with this solution and the wet coated tablets are dried. The dried tablets are then dusted with component 12.

Amlodipine besylate for incorporation into the formulation is prepared as follows:

| | |
|---|---|
| 13. Amlodipine Besylate | 6.944 g |
| 14. Microcrystalline Cellulose | 124.056 g |
| 15. Calcium Phosphate Dibasic | 63.000 g |
| 16. Sodium Starch Glycolate | 4.000 g |
| 17. Magnesium Stearate | 2.000 g |

Components 13–16 are mixed together and the blended mixture is screened and reblended. Component 17 is separately screened and then blended with the reblended mixture containing the amlodipine.

No. 1 hard gelatin capsules are used to encapsulate one benazepril hydrochloride containing coated core along with 200 mg of the amlodipine besylate containing powder per capsule.

We claim:

1. A method of treating a condition selected from the group consisting of hypertension, congestive heart failure, angina, myocardial infarction, artherosclerosis, diabetic nephropathy, diabetic cardiac myopathy, renal insufficiency, peripheral vascular disease, left ventricular hypertrophy, cognitive dysfunction, stroke, and headache, in a human in need thereof, consisting of administering a daily dose of
   (a) benazepril, in free or pharmaceutically acceptable salt form, in an amount corresponding to from 2 mg to 80 mg of benazepril hydrochloride; and
   (b) amlodipine, in free or pharmaceutically acceptable salt form, in an amount corresponding to from 1 mg to 20 mg of amlodipine free base,
wherein the ratio of benazepril to amlodipine corresponds to a weight ratio of from 1:1 to 8:1 of benazepril hydrochloride to amlodipine free base.

2. The method of claim 1 wherein the benazepril and the amlodipine are administered in a single dosage form, such that the benazepril and amlodipine are physically separated from each other.

3. The method of claim 7 wherein the single dosage form comprises a capsule comprising within it (a) a coated compressed tablet of benazepril and (b) amlodipine powder.

4. The method of claim 3 wherein the benazepril is benazepril hydrochloride and the amlodipine is amlodipine besylate.

5. The method of claim 4 wherein the amount of benazepril hydrochloride is 20 mg and the amount of amlodipine besylate corresponds to 5 mg of amlodipine free base.

6. The method of claim 4 wherein the ratio of benazepril to amlodipine corresponds to a weight ratio of benazepril hydrochloride to amlodipine free base of 2:1 or 4:1.

7. The method of claim 6 wherein the ratio of benazepril to amlodipine corresponds to a weight ratio of benazepril hydrochloride to amlodipine free base of 4:1.

8. The method of claim 1 wherein the benazepril is benazepril hydrochloride.

9. The method of claim 1 wherein the amlodipine is amlodipine besylate.

10. The method of claim 1 wherein the benazepril is benazepril hydrochloride and the amlodipine is amlodipine besylate.

11. The method of claim 1 wherein the ratio of benazepril to amlodipine corresponds to a weight ratio of benazepril hydrochloride to amlodipine free base of 1:1, 2:1, 4:1, or 8:1.

12. The method of claim 1 wherein the ratio of benazepril to amlodipine corresponds to a weight ratio of benazepril hydrochloride to amlodipine free base of 2:1.

13. The method of claim 11 wherein the ratio of benazepril to amlodipine corresponds to a weight ratio of benazepril hydrochloride to amlodipine free base of 4:1.

14. The method of claim 1 wherein the daily dosage of benazepril corresponds to from 5 mg to 20 mg benazepril hydrochloride.

15. The method of claim 1 wherein the daily dosage of amlodipine corresponds to from 2.5 mg to 5 mg of amlodipine free base.

16. The method of claim 1 wherein the daily dosage of benazepril corresponds to from 5 mg to 20 mg benazepril hydrochloride and the daily dosage of amlodipine corresponds to from 2.5 mg to 5 mg of amlodipine free base.

17. The method of claim 1 wherein the benazepril is administered in a first formulation which is free of the amlodipine and the amlodipine is administered in a second formulation which is free of the benazepril.

18. The method of claim 17 wherein said first formulation and said second formulation are administered within about one hour of each other.

19. A pharmaceutical composition consisting essentially of a daily dose of
   (a) benazepril, in free or pharmaceutically acceptable salt form, in an amount corresponding to from 2 mg to 80 mg of benazepril hydrochloride; and
   (b) amlodipine, in free or pharmaceutically acceptable salt form, in an amount corresponding to from 1 mg to 20 mg of amlodipine free base,
wherein the ratio of benazepril to amlodipine corresponds to a weight ratio of from 1:1 to 8:1 of benazepril hydrochloride to amlodipine free base, such that the benazepril and the amlodipine are physically separated from one another.

20. The pharmaceutical composition of claim 19 wherein the benazepril is benazepril hydrochloride.

21. The pharmaceutical composition of claim 19 wherein the amlodipine is amlodipine besylate.

22. The pharmaceutical composition of claim 19 wherein the benazepril is benazepril hydrochloride and the amlodipine is amlodipine besylate.

23. The pharmaceutical composition of claim 19 wherein the ratio of benazepril to amlodipine corresponds to a weight ratio of benazepril hydrochloride to amlodipine free base of 1:1, 2:1, 4:1, or 8:1.

24. The pharmaceutical composition of claim 19 wherein the ratio of benazepril to amlodipine corresponds to a weight ratio of benazepril hydrochloride to amlodipine free base of 2:1.

25. The pharmaceutical composition of claim 19 wherein the ratio of benazepril to amlodipine corresponds to a weight ratio of benazepril hydrochloride to amlodipine free base of 4:1.

26. The pharmaceutical composition of claim 19 wherein the amount of benazepril corresponds to from 5 mg to 20 mg benazepril hydrochloride.

27. The pharmaceutical composition of claim 19 wherein the amount of amlodipine corresponds to from 2.5 mg to 5 mg of amlodipine free base.

28. The pharmaceutical composition of claim 19 wherein the amount of benazepril corresponds to from 5 mg to 20 mg benazepril hydrochloride and the amount of amlodipine corresponds to from 2.5 mg to 5 mg of amlodipine free base.

29. The pharmaceutical composition of claim 19 in the form of capsule comprising within it (a) a coated compressed tablet of benazepril, and (b) amlodipine powder.

30. The pharmaceutical composition of claim 19 wherein the benazepril is benazepril hydrochloride and the amlodipine is amlodipine besylate.

31. The pharmaceutical composition of claim 30 wherein the amount of benazepril hydrochloride is 20 mg and the amount of amlodipine besylate corresponds to 5 mg of amlodipine free base.

32. The pharmaceutical composition of claim 29 wherein the ratio of benazepril to amlodipine corresponds to a weight ratio of benazepril hydrochloride to amlodipine free base of 2:1 or 4:1.

33. The pharmaceutical composition of claim 32 wherein the ratio of benazepril to amlodipine corresponds to a weight ratio of benazepril hydrochloride to amlodipine free base of 4:1.

* * * * *

UNITED STATES PATENT AND TRADEMARK OFFICE
CERTIFICATE OF CORRECTION

PATENT NO. : 6,162,802
DATED : December 19, 2000
INVENTOR(S) : Papa et al.

It is certified that error appears in the above-identified patent and that said Letters Patent is hereby corrected as shown below:

Column 5,
Line 8, "artheroscierosis" should read -- atherosclerosis --.

Column 5, claim 3,
Line 26, "claim 7" should read -- claim 2 --.

Column 5, claim 12,
Line 52, "claim 1" should read -- claim 11 --.

Column 6, claim 30,
Line 52, "claim 19" should read -- claim 29 --.

Signed and Sealed this

Twentieth Day of November, 2001

Attest:

*Attesting Officer*

NICHOLAS P. GODICI
*Acting Director of the United States Patent and Trademark Office*